(12) United States Patent
Banik et al.

(10) Patent No.: US 10,583,240 B2
(45) Date of Patent: Mar. 10, 2020

(54) MEDICAL CANNULA PACKAGE

(71) Applicant: Becton, Dickinson and Company, Franklin Lakes, NJ (US)

(72) Inventors: Robert Banik, Edgewater, NJ (US); Peter Skutnik, Midland Park, NJ (US); Sean Sullivan, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 269 days.

(21) Appl. No.: 15/614,519

(22) Filed: Jun. 5, 2017

(65) Prior Publication Data
US 2017/0266366 A1 Sep. 21, 2017

Related U.S. Application Data

(63) Continuation of application No. 14/378,080, filed as application No. PCT/US2013/025752 on Feb. 12, 2013, now Pat. No. 9,694,129.

(60) Provisional application No. 61/598,186, filed on Feb. 13, 2012.

(51) Int. Cl.
| | |
|---|---|
| *A61M 5/32* | (2006.01) |
| *B65B 5/04* | (2006.01) |
| *A61M 5/00* | (2006.01) |
| *A61M 5/34* | (2006.01) |
| *A61M 5/24* | (2006.01) |

(52) U.S. Cl.
CPC .......... *A61M 5/002* (2013.01); *A61M 5/3204* (2013.01); *B65B 5/04* (2013.01); *A61M 5/3202* (2013.01); *A61M 5/3213* (2013.01); *A61M 5/347* (2013.01); *A61M 2005/2474* (2013.01); *A61M 2207/00* (2013.01)

(58) Field of Classification Search
CPC .............. A61M 5/24; A61M 2205/581; A61M 5/31541; A61M 2205/582; A61M 5/3202; A61M 5/002; B65B 5/04; B65B 9/045; B65B 11/52; B65D 85/24; B65D 83/02; B65D 2205/00
USPC .................................. 53/467, 246, 471, 271
See application file for complete search history.

(56) References Cited

U.S. PATENT DOCUMENTS

| | | | |
|---|---|---|---|
| 2,953,243 A | 9/1960 | Roehr | |
| 3,036,700 A | 5/1962 | Krug | |
| 3,074,540 A | 1/1963 | Beich et al. | |
| 3,625,353 A * | 12/1971 | Ishii | A61L 2/26 206/365 |
| 4,113,090 A * | 9/1978 | Carstens | A61M 5/3202 206/210 |
| 4,610,667 A | 9/1986 | Pedicano et al. | |

(Continued)

FOREIGN PATENT DOCUMENTS

| | | |
|---|---|---|
| EP | 2201976 A1 | 6/2010 |
| GB | 920341 A | 3/1963 |

(Continued)

*Primary Examiner* — Hemant Desai
*Assistant Examiner* — Jacob A Smith
(74) *Attorney, Agent, or Firm* — Dickinson Wright PLLC

(57) ABSTRACT

A package for a medical cannula with a hub, such as a pen needle, is disclosed. The package includes a cover for receiving a medical cannula and for engaging a hub of the medical cannula. The cover has open ends that are in communication through the cover. The packaging also includes a sterility barrier for the cover.

13 Claims, 13 Drawing Sheets

(56) References Cited

U.S. PATENT DOCUMENTS

| | | | |
|---|---|---|---|
| 4,750,318 A * | 6/1988 | Matsuzawa | B26D 3/085 53/559 |
| 4,883,470 A * | 11/1989 | Haindl | A61M 5/3213 604/192 |
| 4,932,418 A | 6/1990 | Coburn | |
| 5,230,428 A * | 7/1993 | McShane | A61M 5/3213 206/363 |
| 5,545,145 A | 8/1996 | Clinton et al. | |
| 5,735,827 A * | 4/1998 | Adwers | A61M 5/3213 604/192 |
| 5,769,826 A | 6/1998 | Johnson | |
| 5,807,374 A | 9/1998 | Caizza et al. | |
| 5,873,462 A * | 2/1999 | Nguyen | A61M 5/002 206/366 |
| 5,944,700 A * | 8/1999 | Nguyen | A61M 5/46 604/117 |
| 5,968,021 A * | 10/1999 | Ejlersen | A61M 5/3213 206/365 |
| 5,971,966 A * | 10/1999 | Lav | A61M 5/002 206/365 |
| 6,059,758 A | 5/2000 | Padilla et al. | |
| 6,159,193 A * | 12/2000 | Turk | A61M 5/002 604/411 |
| 6,206,855 B1 * | 3/2001 | Kunkel | A61M 5/3213 206/365 |
| 6,248,095 B1 | 6/2001 | Giambattista et al. | |
| 6,488,666 B1 | 12/2002 | Geist | |
| 6,591,984 B2 | 7/2003 | Odierno et al. | |
| 6,889,830 B2 | 5/2005 | Bergerson et al. | |
| 7,591,122 B2 * | 9/2009 | Monti | B65B 5/103 53/246 |
| 7,645,264 B2 | 1/2010 | Marsh et al. | |
| 7,891,487 B2 * | 2/2011 | Erickson | B65D 85/24 206/366 |
| 8,133,202 B2 | 3/2012 | Marsh | |
| 8,491,535 B2 | 7/2013 | Limaye | |
| 9,186,452 B2 | 11/2015 | DiBiasi | |
| 2002/0014430 A1 * | 2/2002 | Groth | A61M 5/002 206/438 |
| 2002/0020647 A1 * | 2/2002 | Groth | A61M 5/002 206/366 |
| 2003/0121812 A1 * | 7/2003 | Sprieck | A61B 17/205 206/365 |
| 2003/0168376 A1 * | 9/2003 | Taneja | B65B 9/045 206/534 |
| 2004/0064095 A1 * | 4/2004 | Vitello | A61M 5/3134 604/111 |
| 2010/0063457 A1 | 3/2010 | Crossman | |
| 2010/0185178 A1 | 7/2010 | Sharp et al. | |
| 2011/0071475 A1 | 3/2011 | Horvath et al. | |
| 2011/0290799 A1 * | 12/2011 | Anderson | A61M 5/31511 220/200 |
| 2012/0029440 A1 * | 2/2012 | Boyd | A61M 5/002 604/192 |
| 2013/0066271 A1 | 3/2013 | West | |

FOREIGN PATENT DOCUMENTS

| | | |
|---|---|---|
| GB | 2437923 A | 11/2007 |
| JP | S33-019484 | 11/1958 |
| JP | H08276015 | 10/1996 |
| JP | H10-502551 | 3/1998 |
| JP | H11114064 | 4/1999 |
| JP | H11-137687 | 5/1999 |
| JP | 2001-286562 | 10/2001 |
| JP | 2005-199059 | 7/2005 |
| JP | 3131804 | 4/2007 |
| JP | 2009-536539 | 10/2009 |
| JP | 2011-062527 | 3/2011 |
| JP | 2012-232136 | 11/2012 |
| WO | WO-2011/107330 A1 | 9/2011 |
| WO | WO-2011146042 A1 | 11/2011 |
| WO | WO-2016/024085 | 2/2016 |

* cited by examiner

MEDICAL CANNULA PACKAGE

CROSS-REFERENCE TO RELATED APPLICATION

This application is a continuation of U.S. patent application Ser. No. 14/378,080, filed on Aug. 11, 2014, which is the U.S. national stage of International Application No. PCT/US2013/025752, filed on Feb. 12, 2013, which claims the benefit of U.S. Provisional Application No. 61/598,186, filed on Feb. 13, 2012, the disclosures of which are incorporated herein by reference in their entirety.

BACKGROUND OF THE INVENTION

1. Field of the Invention

The present invention relates to medical cannula packaging, and more particularly, to packaging for dispensing and storing a medical cannula.

2. Description of the Related Art

Medication delivery pens are used for self-injection of precisely measured doses of medication. Pens are widely used, for example, by diabetics to self-inject insulin. A typical medication delivery pen includes a cartridge which contains a volume of liquid medication sufficient for several doses. Using a disposable pen needle attached to the pen device, the dose is injected into a tissue area, such as the intramuscular tissue layer, the subcutaneous tissue layer, or the intradermal tissue layer.

Pen injection devices, such as the exemplary pen injector 50 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the exemplary drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein because they are understood by one of ordinary skill in the art.

A pen needle assembly 10 includes a hub 20, a hollow patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is preferably threaded onto the lower housing 17, although other attachment means can be used such as attaching directly to the medicament cartridge 12. In attaching the hub 20 to the lower housing 17 or medicament cartridge 12, the septum-penetrating cannula 18 pierces the septum 16, but the septum 16 does not move with respect to the medicament cartridge 12. The stopper 15, however, is axially displaceable within the medicament cartridge 12 while maintaining a fluid-tight seal. The distal movement of the plunger or stopper 15 within the medicament cartridge 12 (due to advancement of the lead screw 7) causes medication to be forced into the patient needle 11 of the hub 20.

To protect a user, or anyone who handles the pen injector 50, pen needle assemblies are usually individually packaged inside a plastic cover with a peelable label covering the opening in the cover to provide a sterility barrier. For example, a rigid outer shield 29 attaches to and covers the hub 20. The outer shield 29 can also be used as a handle or grip to screw the hub 20 onto or off of the pen injector 50. Typically, a teardrop-shaped cover or label 32 provides a sterility barrier for the contents of the outer shield 29. The label 32 attaches to a top flange 30 of the outer shield 29 and has a tab 34 serving as a handle (shown in FIG. 5). An inner shield or needle cover 28 covers the patient needle 11 within the outer shield 29. The inner shield 28 can be secured to the hub 20 to cover the patient needle 11 by any suitable means, such as an interference fit or a snap fit. The outer shield 29 and inner shield 28 are removed prior to use. The cap 21 fits snugly against outer sleeve 13 to allow a user to securely carry the pen injection device 50.

Individually packaged pen needle assemblies are often sold packed loosely in a container, such as a box. Boxes of various sizes are used for various quantities of the individually packaged pen needle assemblies (for example, a 50-count box or a 100-count box).

SUMMARY OF EMBODIMENTS OF THE INVENTION

It is an aspect of the present invention to provide packaging for dispensing and storing medical cannulas. More specifically, it is an aspect of the present invention to provide packaging for dispensing and storing medical needles, for example, pen needles, prior to their use as well as subsequent to their use. Additionally, it is an aspect of the present invention to provide a method of packaging medical needles for use with an injection device, such as a pen injection device.

The foregoing and/or other aspects of the present invention are achieved by providing a package for a medical cannula having a hub. The package includes a cover for receiving a medical cannula and for engaging a hub of the medical cannula. The cover has open ends that are in communication through the cover. The packaging also includes a sterility barrier for the cover.

The foregoing and/or other aspects of the present invention are also achieved by providing a package for a medical cannula having a hub. The package includes a cover for receiving a medical cannula and for securing therein a hub of the medical cannula. The package also includes a sterility barrier for encasing the cover, a hub and its medical cannula.

The foregoing and/or other aspects of the present invention are also achieved by providing a method of packaging a medical cannula having a hub. The method includes providing a cover for receiving a medical cannula and for securing a hub of the medical cannula therein, inserting the medical cannula into the cover, and providing a sterility barrier for the cover with the medical cannula and hub disposed therein.

Additional and/or other aspects and advantages of the present invention will be set forth in part in the description that follows and, in part, will be apparent from the description, or may be learned by practice of the invention.

BRIEF DESCRIPTION OF THE DRAWINGS

The above and/or other aspects and advantages of embodiments of the invention will become apparent and more readily appreciated from the following detailed description, taken in conjunction with the accompanying drawings, in which.

DETAILED DESCRIPTION OF EMBODIMENTS OF THE PRESENT INVENTION

Figure 1:
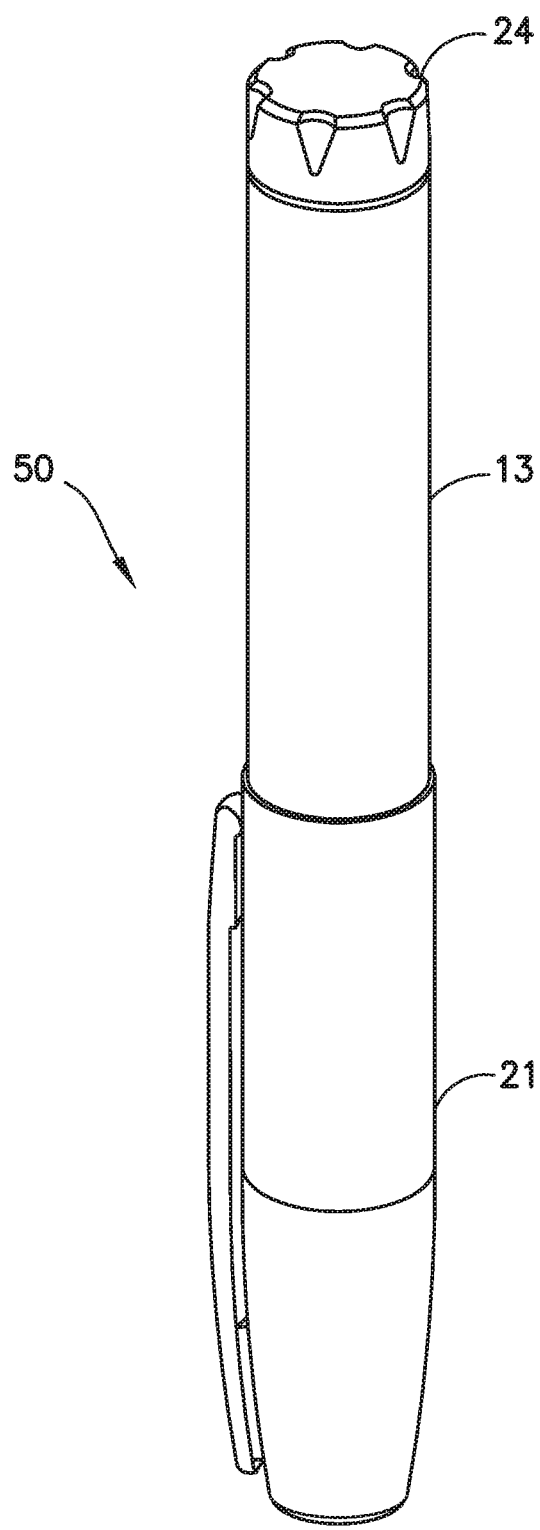
FIG. 1 is a perspective view of an exemplary drug delivery pen.
Figure 2:
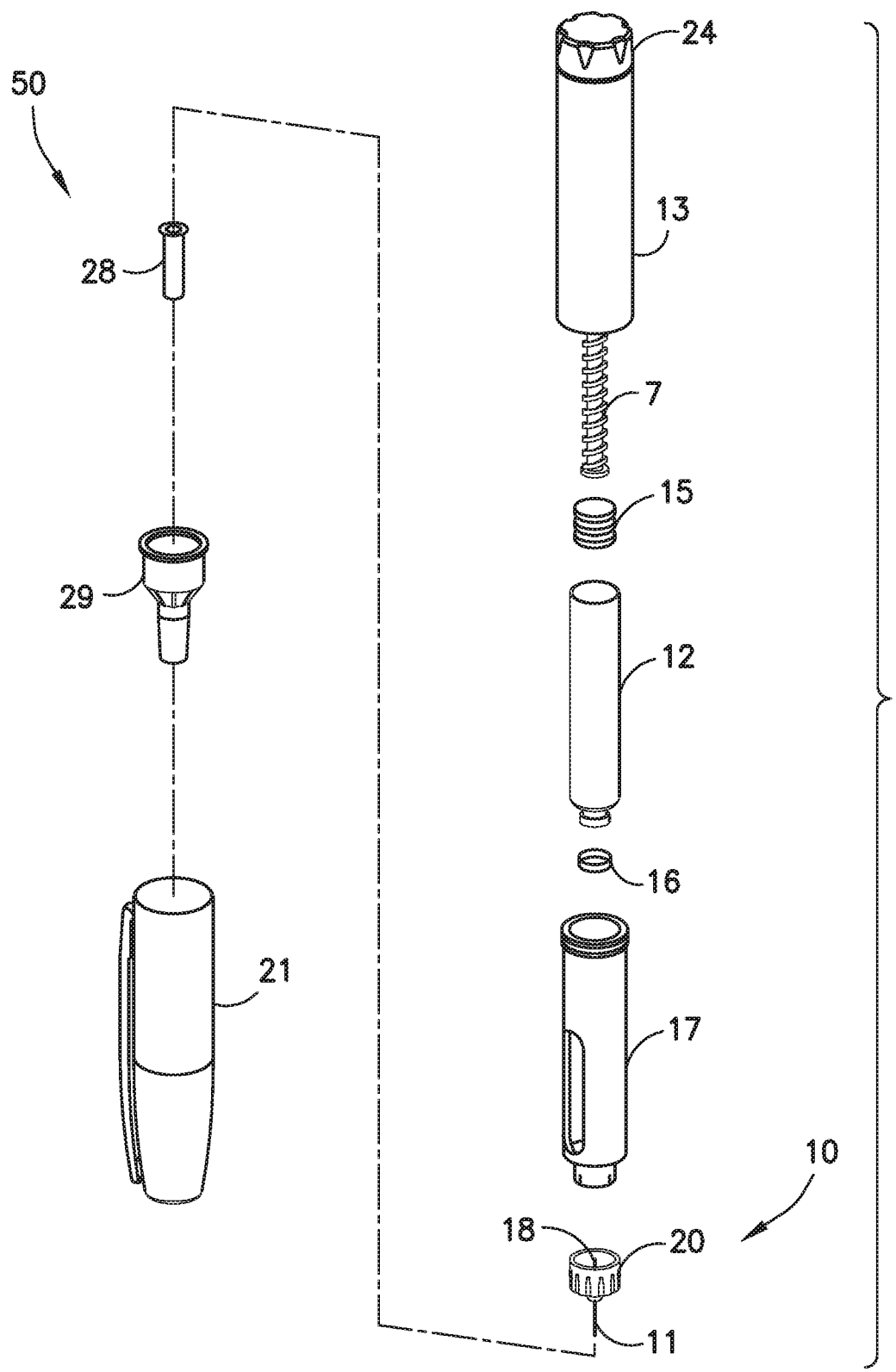
FIG. 2 is an exploded view of the exemplary drug delivery pen of FIG. 1.

Reference will now be made in detail to embodiments of the present invention, examples of which are illustrated in the accompanying drawings, wherein like reference numerals refer to the like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 3:
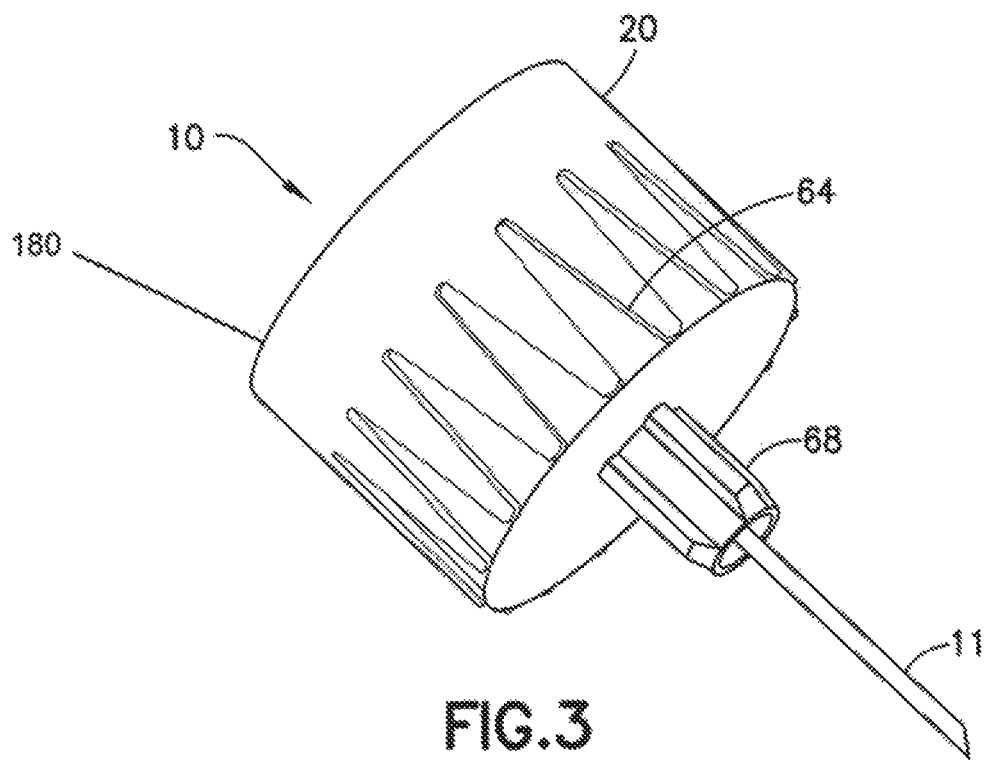
FIGS. 3 and 4 are perspective views of a pen needle assembly that can be used in embodiments of the present invention.
Figure 4:
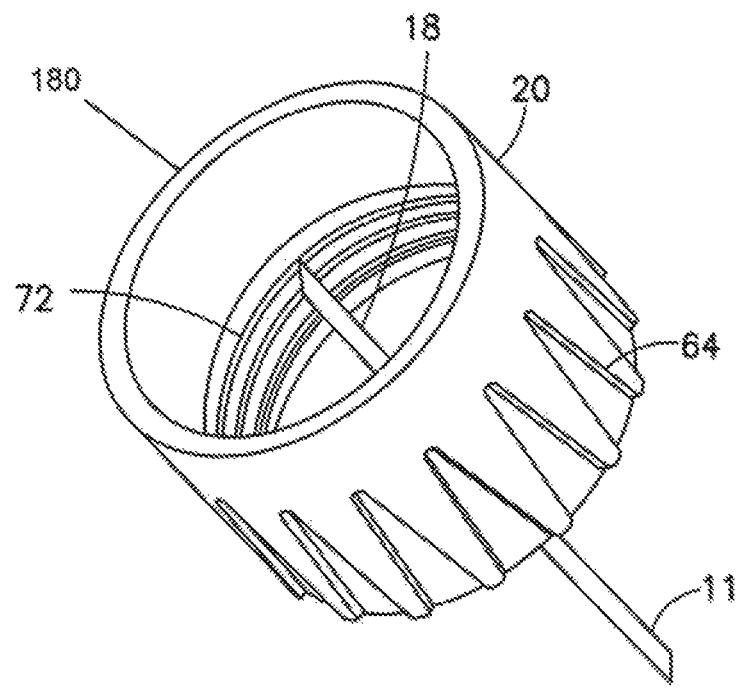
Figure 5:
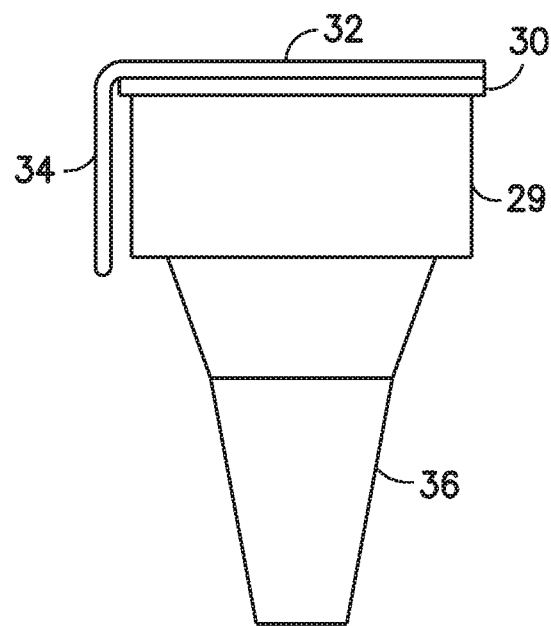
FIG. 5 is a perspective view of an outer shield for the pen needle assembly of FIGS. 3 and 4.

FIGS. 3 and 4 are perspective views of a pen needle assembly 10 that can be used in embodiments of the present invention. For brevity, the phrase "pen needle 10" will be used hereinafter instead of "pen needle assembly 10." As shown in FIG. 3, the pen needle 10 includes a plastic hub 20 disposed at a non-patient end thereof. The hub 20 includes a plurality of ribs 64 for engagement with anti-rotation/retaining structures that will be described in greater detail below. In addition, protrusion 68 extends from a patient end of the hub 20 and the hollow patient needle 11 extends from the protrusion 68. The septum-penetrating metal needle cannula 18 (best shown in FIG. 4) disposed within the non-patient end of the hub 20 fluidly communicates with the patient needle 11. Further, as shown in FIG. 4, the interior of the non-patient end of the hub 20 includes threads 72 for connection with an injection device, such as the pen injector 50. For brevity, hereinafter, the pen injector 50 will be employed as an exemplary injection device. One skilled in the art, however, will appreciate that other types of injection devices may be used without departing from the scope of the present invention. FIG. 5 is a perspective view of a typical outer shield 29 for the pen needle assembly of FIGS. 3 and 4.

Figure 6:
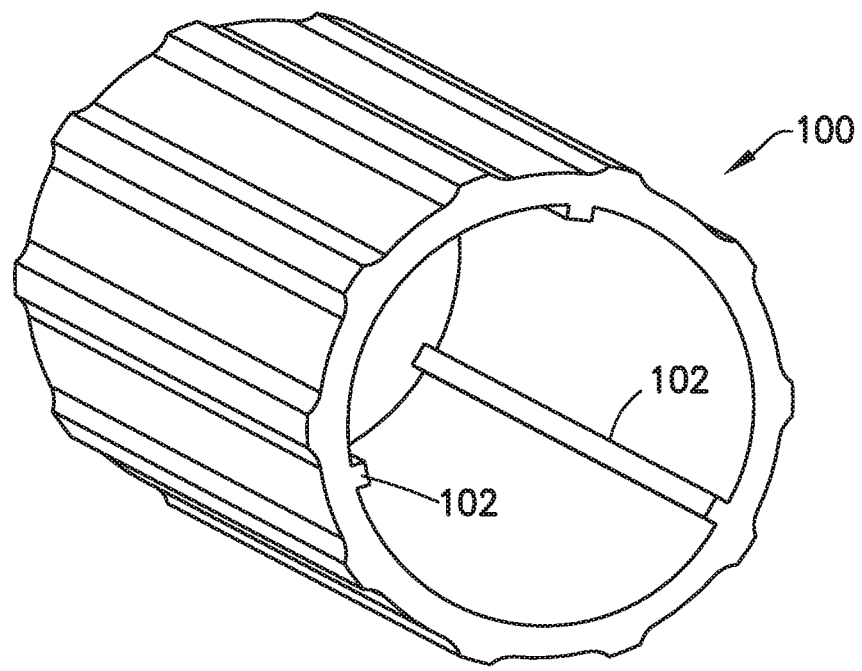
FIG. 6 is a perspective view of a cover in accordance with an embodiment of the present invention.
Figure 7:
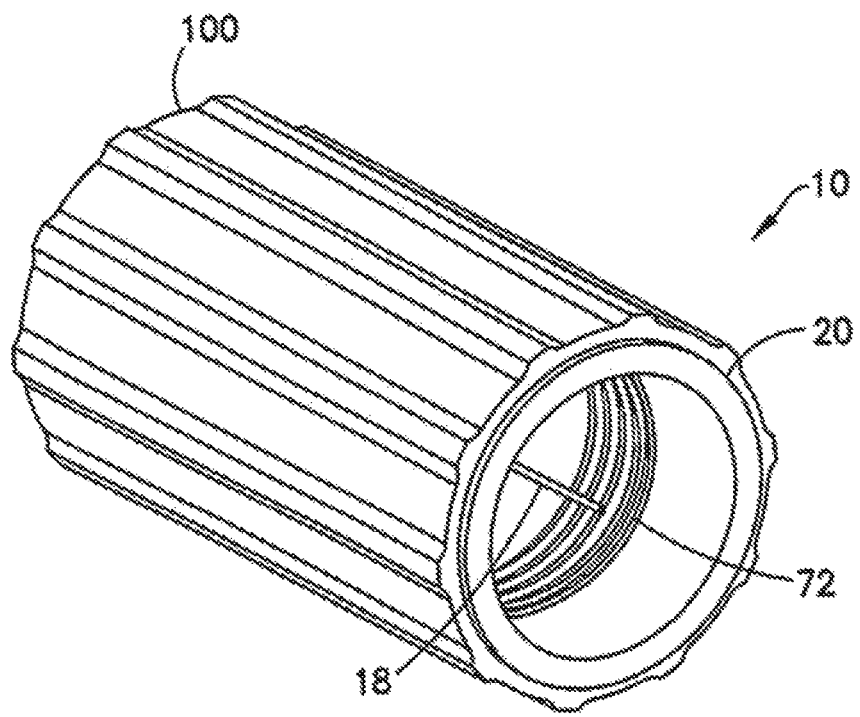
FIG. 7 is a perspective view of the cover of FIG. 6 mated with the pen needle assembly of FIGS. 3 and 4.

FIG. 6 is a perspective view of a cover 100 in accordance with an embodiment of the present invention. The cover 100 receives and selectively engages with an exterior (i.e., the hub 20) of a pen needle 10, as shown in FIG. 7. More specifically, according to one embodiment, the cover 100 includes a plurality of radially inward protrusions or splines 102 for selectively engaging the hub 20 of the pen needle 10. For example, when inserted into the cover 100, the spaces between the ribs 64 on the hub 20 of the pen needle 10 engage the splines 102. While permitting relative axial displacement, the engagement between the hub 20 and the splines 102 prevents rotation of the pen needle 10 relative to the cover 100. This facilitates engagement and disengagement of the pen needle 10 with the pen injector 50. Particularly, the increased external surface area of the cover 100 (relative to the pen needle 10 or the outer shield 29) provides increased gripping area for a user.

According to one embodiment, the interior of the cover 100 has a shape that corresponds to the shape of the hub 20. As shown in FIGS. 3, 4, 6, and 7, the hub 20 of the pen needle 10 and the cover 100 are substantially cylindrical. One skilled in the art will appreciate, however, that other shapes can be used without departing from the scope of the present invention. For example, the hub 20 and the interior of the cover 100 can have 3, 4, 5, or more corresponding facets. As with the splines 102, such an embodiment prevents relative rotation of the pen needle 10 and the cover 100. As another example, the hub 20 of the pen needle can include a plurality of facets and the cover 100 can include a greater plurality of facets, thereby permitting multiple orientations of the pen needle 10 with respect to the cover 100, while still preventing relative rotation of the pen needle 10 and the cover 100. As other examples, the pen needle and cover can be round and faceted, or even round with a single facet.

According to one embodiment, the cover 100 is open-ended, i.e., the cover 100 has openings at ends thereof. More specifically, in the embodiment shown in FIG. 6, the cylindrical cover 100 has openings at both opposing ends thereof. Such an embodiment, unlike the outer cover 29 of FIG. 5, permits insertion of the pen needle 10 into either end of the cover 100. One skilled in the art, however, will appreciate that other configurations can be used without departing from the scope of the present invention. For example, although the cover 100 depicted in FIG. 6 is a substantially straight cylinder, the cover 100 can be segmented, or curved, such that the ends of the cover 100 do not oppose each other.

While the shape of the cover 100 shown in FIG. 6 allows it to be molded, the cover 100 can also be extruded, thereby reducing the time to manufacture the cover 100. Polypropylene is an example of a plastic that can be used to make the cover 100, although one skilled in the art will appreciate that other plastics and other materials can be used without departing from the scope of the present invention.

Employing the cover 100 shown in FIG. 6, a user can grasp the cover 100 and use it to connect an injection device, such as the injection pen 50, to the enclosed pen needle 10, for example, by threading the pen injector 50 into the non-patient end of the pen needle 10. Once connected, the user can pull on the pen injector while still grasping the cover 100 to remove the pen needle 10 from the cover, thereby exposing the patient end of the pen needle 10 for injection. According to one embodiment, the cover 100 is flexible or deformable, and the user's grasping of the cover 100 can help prevent the pen needle 10 from rotating during connection to the injection device. According to another embodiment, the cover 100 is substantially rigid. Subsequent to the injection, the user can return the pen needle 10 to the cover 100 by grasping the cover and inserting the used needle. If desired, the user can leave the pen needle 10 connected to the pen injector 50. Alternatively, the user can grasp the cover, and unthread the pen injector 50 from the pen needle. In this state, the user can again access the used pen needle 10 in the cover 100 if desired.

Figure 8:
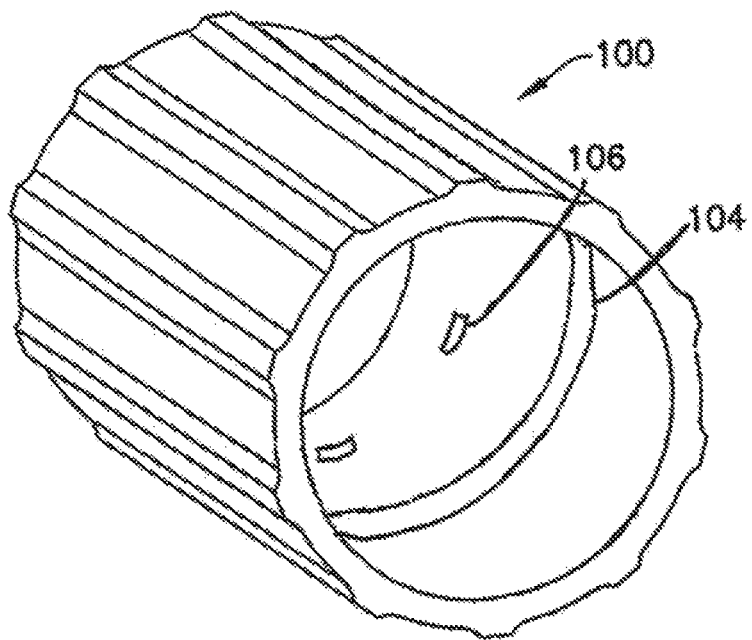
FIG. 8 is a perspective view of a cover with a lockout feature according to an embodiment of the present invention.
Figure 16:
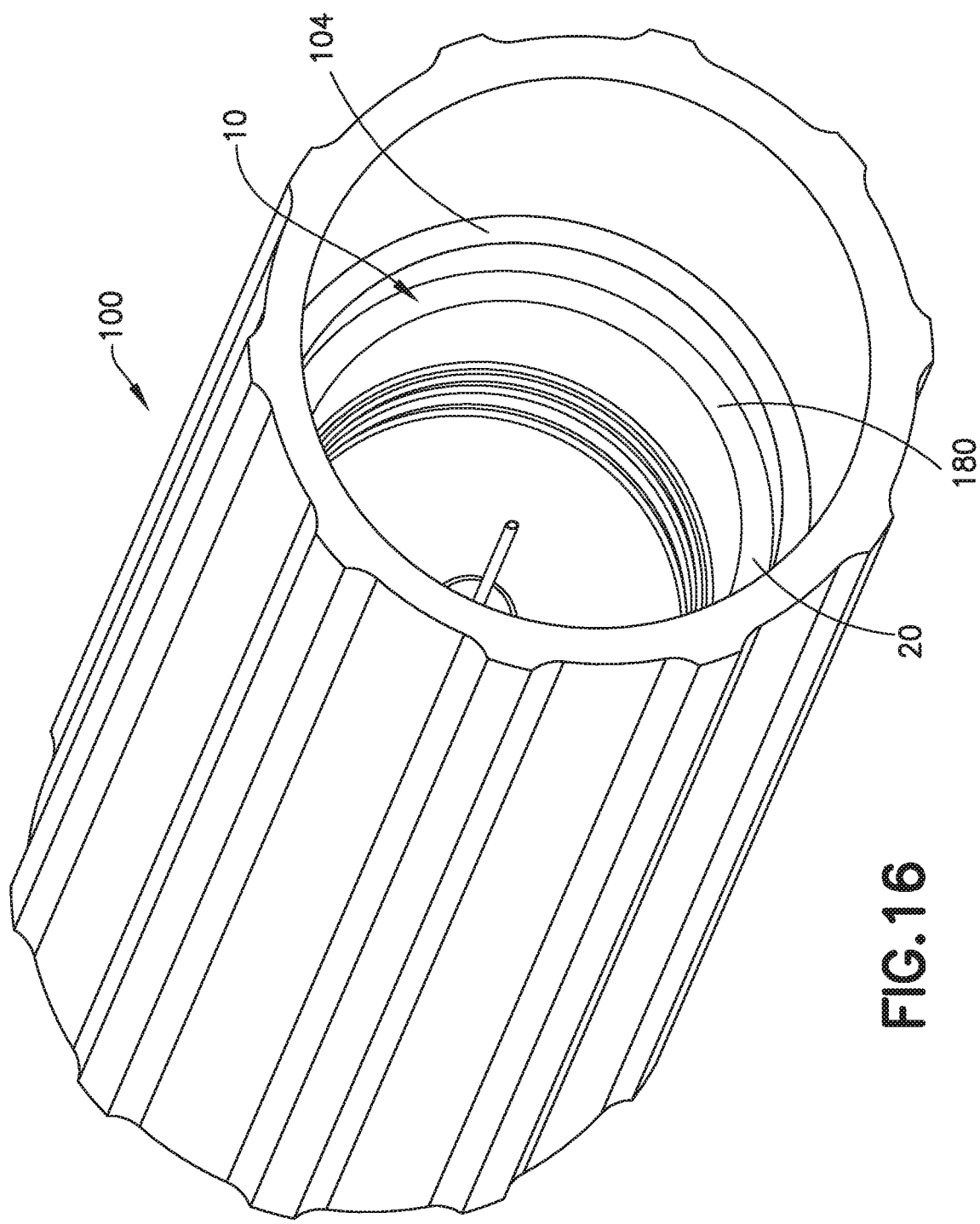
FIG. 16 is a perspective view of the cover of FIG. 8 with the pen needle assembly of FIG. 3 disposed therein.

According to an alternative embodiment shown in FIG. 8, the cover 100 includes a lock-out feature 104 that holds or retains the used pen needle 10 after being returned to the cover 100, thereby preventing re-use of the pen needle 10. The lock-out feature 104 can be an integral internal shoulder, bump, ledge, or flap, and can be continuous or discontinuous around the inner surface of the cover 100. Tolerances of the fit between the pen needle 10 and the cover 100 can be adjusted so that the force required by a user to insert the used pen needle 10 into the cover would result in the proximal end 180 (see FIGS. 3 and 4) of the hub 20 passing the lock-out feature 104 (see FIG. 16), and thereby subsequently preventing the pen needle 10 from being removed from the cover 100. According to one embodiment, the cover 100 also includes a stop 106 to prevent the used pen needle 10 from being inserted so far that the needle 11 presents a danger from the other side of the cover 100. According to another embodiment, a shoulder of the pen injector 50 can be used to limit insertion depth of the pen needle relative to the cover 100.

Figure 9:
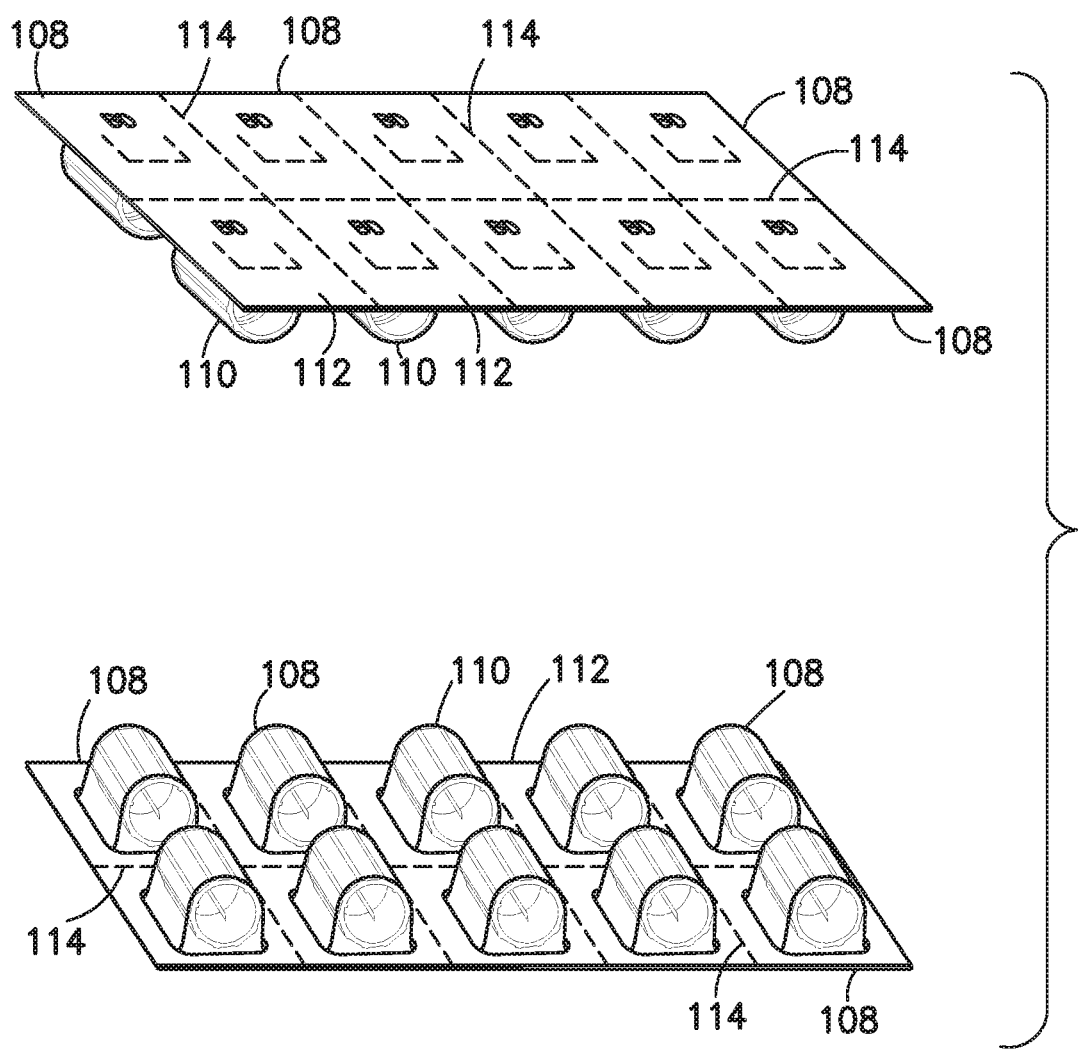
FIG. 9 is a perspective view of a pair of arrays of blister pack sterility barriers according to an embodiment of the present invention.
Figure 10:
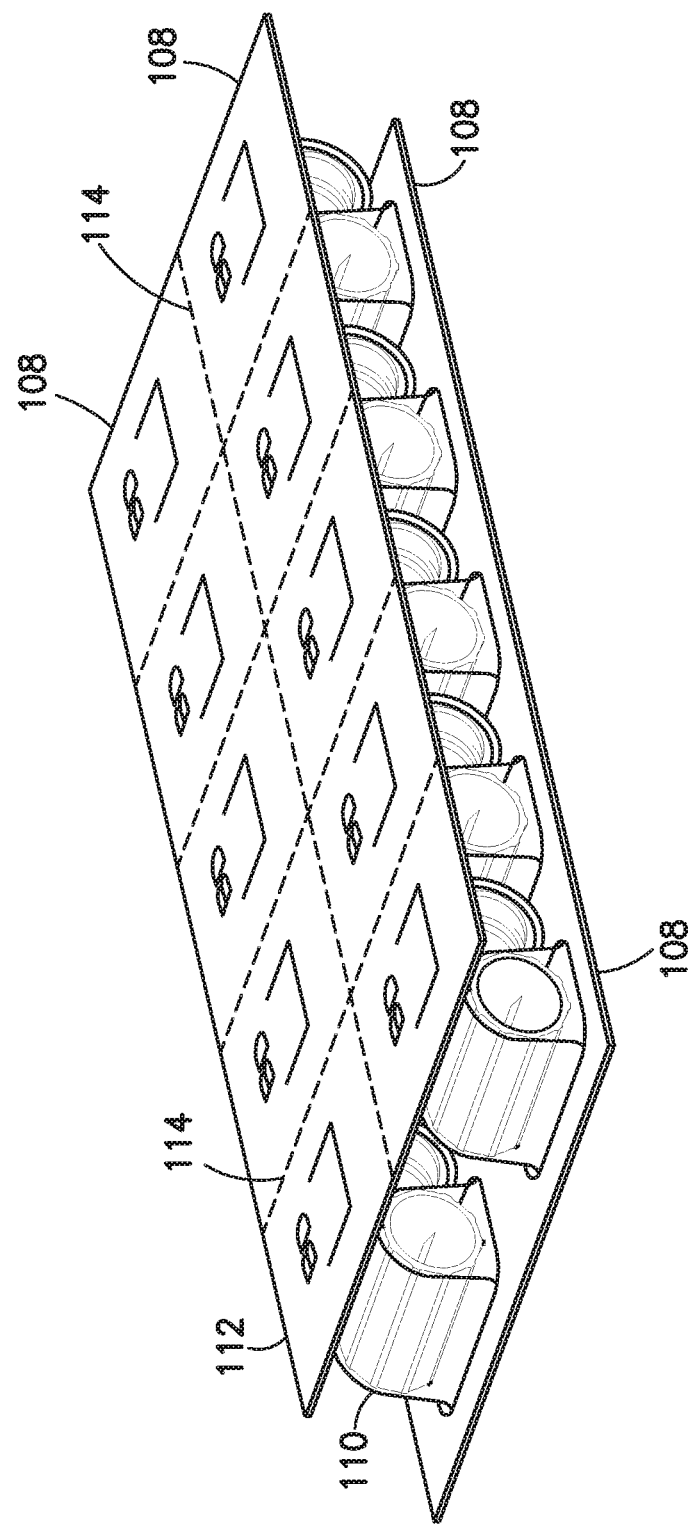
FIG. 10 is a perspective view of the arrays of blister pack sterility barriers of FIG. 9 nested together.

Embodiments of the present invention can also include a sterility barrier for enclosing the cover 100 with the pen needle therein. According to one embodiment, the sterility barrier includes a blister pack sterility barrier 108. For brevity, the blister pack sterility barrier 108 will be referred to as the blister pack 108. FIG. 9 illustrates respective top and bottom views of a pair of blister pack arrays, and FIG. 10 illustrates the arrays in a nested configuration, for example, for transport or for packing in a container. Each blister pack 108 includes a blister portion 110 that is formed to accommodate the combined cover 100 and pen needle 10, and a lid portion 112 to seal the blister portion 110.

The blister portion 110 can be made of transparent flexible plastic, although other materials can be used without departing from the scope of the present invention. Additionally, the blister portion 110 can be pre-formed, for example, by thermoforming. Alternatively, the combined pen needle 10 and cover 100 can be pressed in to form the blister portion 110. The lid portion 112 can be made of paper, plastic, foil, or a combination of materials. Additionally, the lid portion, and individually seals each blister portion 110, and thus, in an array, each combined cover 100 and pen needle 10 is sterile, and is separated from the remaining combined pen needles 10 and covers 100.

Preferably, the blister pack arrays are scored or perforated at 114, as shown in FIG. 9, so that each blister pack 108 is individually separable from the array. This allows the user to select and remove a single blister pack 108 or a subset of blister packs 108 from the array, so that the user does not have to transport the entire array.

Figure 11:
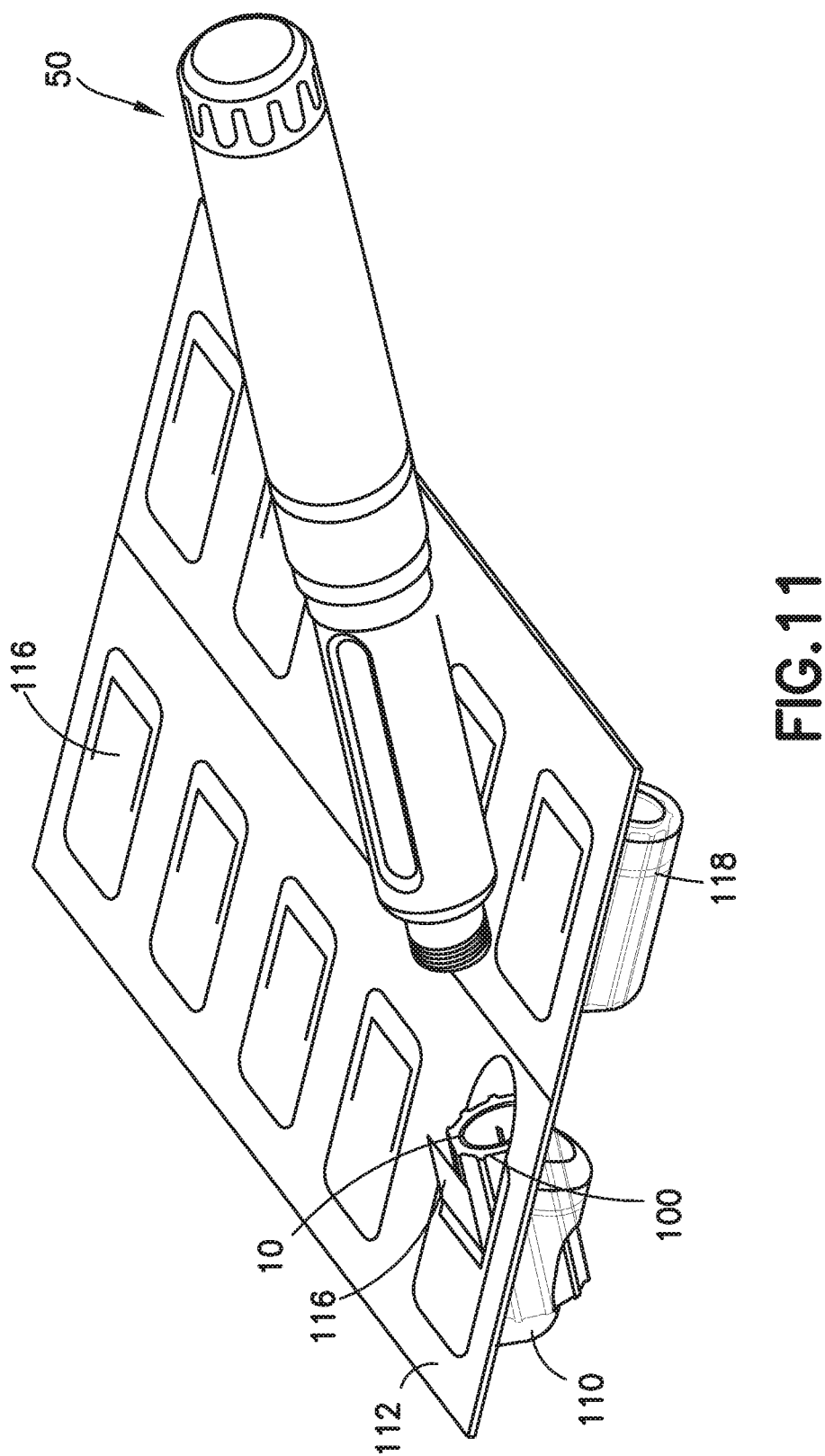
FIG. 11 is a perspective view of an array of blister pack sterility barriers of FIG. 9 with a pen needle of FIGS. 3 and 4 ready for connection with a drug delivery pen of FIGS. 1 and 2.

According to one embodiment, as shown in FIG. 11, the lid portion 112 has a flap 116 with a scored, perforated, or otherwise weakened perimeter. In this embodiment, to access the pen needle 10, the user presses the blister portion 110 so that the combined pen needle 10 and cover 100 "pop" through the flap 116, thereby exposing the non-patient end of the pen needle 10. As an alternative, the user may peel back the lid portion to expose the combined cover 100 and pen needle 10. To connect the pen needle 10 to the pen injector, according to one embodiment, the user removes the cover 100 from the blister pack and proceeds as previously described. Subsequent to the injection and storage of the pen needle 10 in the cover 100, the user can reinsert the cover into the blister pack for storage or disposal.

According to another embodiment, because of the flexibility of the blister portion 110, the user grasps the blister portion to hold the cover 100 while threading the pen injector 50 into the pen needle 10, or vice versa. Removal of the pen needle 10 from the cover 100, and its return subsequent to injection can proceed as previously described, except that the user again grasps the blister portion 110 instead of directly grasping the cover 100. For storage or disposal, subsequent to the insertion of the used pen needle 10 in the cover 100 and the disconnection of the pen needle 10 from the pen injector 50, the user can push the cover 100 into the flexible blister portion 110 so that the patient end of the pen needle 10 is at least partially covered by the blister portion 110, and therefore, is not easily accessible.

According to another embodiment, the cover 100 remains trapped in the blister portion 108. For example, in one embodiment, each blister portion 108 includes an internal rib 118 to grasp the cover 100. To connect the pen needle 10 to the pen injector 50, the user can grasp the blister portion 110 or another portion of the array, and thread the pen injector 50 into the pen needle 10 or vice versa, because the cover 100 is retained in the blister portion 110 by the internal rib 118. The user then pulls the pen injector with the attached pen needle 10 to expose the patient end of the pen needle and permit injection. Subsequent to the injection, the user re-inserts the pen needle into the cover 100 while holding either the blister portion 100 or another portion of the array, and unthreads the pen needle 10 from the pen injector 50. For storage or disposal, subsequent to the insertion of the pen needle 10 in the cover 100 and the disconnection of the pen needle 10 from the pen injector 50, the user can push the cover 100 into the flexible blister portion 110 so that the patient end of the pen needle 10 is at least partially covered by the blister portion 110, and therefore, is not easily accessible.

According to another embodiment, the cover 100 is selectively retained in the blister portion 108 by the internal rib 118 of the blister portion 108. In this embodiment, the user can overcome the grasp of the rib 118 and "pop" the cover 100 out of the blister portion 108 to grasp the cover 100. Connection to the pen injector, injection, and return of the pen needle 10 to the cover 100 can occur as previously described. For storage or disposal, subsequent to the insertion of the pen needle 10 in the cover 100 and the disconnection of the pen needle 10 from the pen injector 50, the user can push the cover 100 into the flexible blister portion 110 so that the internal rib 118 re-engages the cover 100, thereby retaining the cover 100 within the blister portion 108.

Figure 12:
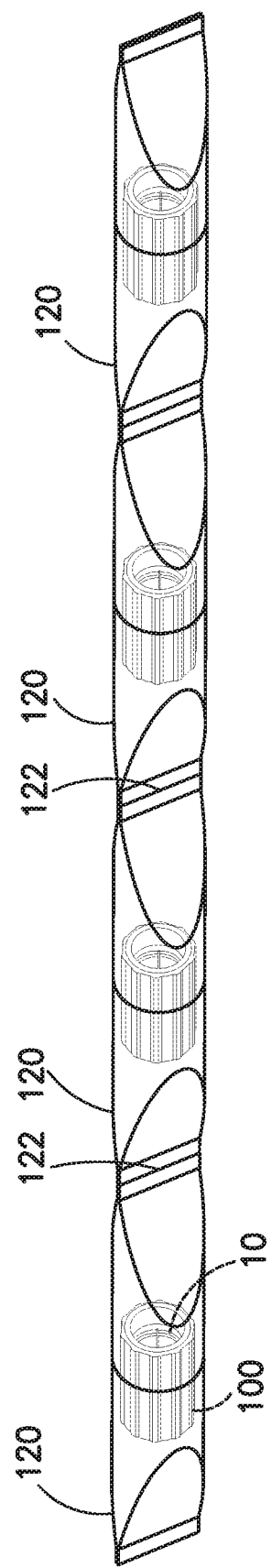
FIG. 12 is a perspective view of an array of flow wrap sterility barriers in accordance with an embodiment of the present invention.

As shown in FIG. 12, in another embodiment, the sterility barrier includes an individually sealed wrapper. According to one embodiment, the wrapper is a transparent plastic wrap, or flow wrap sterility barrier 120. For brevity, the flow wrap sterility barrier 120 will hereinafter be referred to as the flow wrap 120. One skilled in the art will appreciate that the flow wrap 120 need not be transparent, and can be opaque without departing from the scope of the present invention. As an alternative to plastic, paper, foil, or a combination of materials can be used to form the flow wrap 120. According to one embodiment, a plurality of flow wraps 120 separated by crimped or bonded areas are serially connected in an array or strip. Thus, in an array or strip, each combined cover 100 and pen needle 10 are sterile, and are separated from the remaining combined pen needles 10 and covers 100. According to one embodiment, perforations 122 separate the individual flow wraps 120. This permits a user to select a desired number of combined covers 100 and pen needles 10 to transport.

To access the pen needle, 10, the user tears open an individual flow wrap 120, thereby exposing the non-patient end of the pen needle in the cover 100. The user then either removes the cover 100 from the flow wrap 120 and grasps the cover 100 directly, or grasps the cover 100 through the flow wrap 120, and subsequently threads the pen injector into the pen needle 10 or vice versa. During the re-insertion of the pen needle 10 into the cover 100 subsequent to the injection, the user can either grasp the cover 100 directly, or grasp the cover 100 through the flexible flow wrap 120, and then disconnect the pen injector 50 from the pen needle 10 as previously described.

Figure 13:
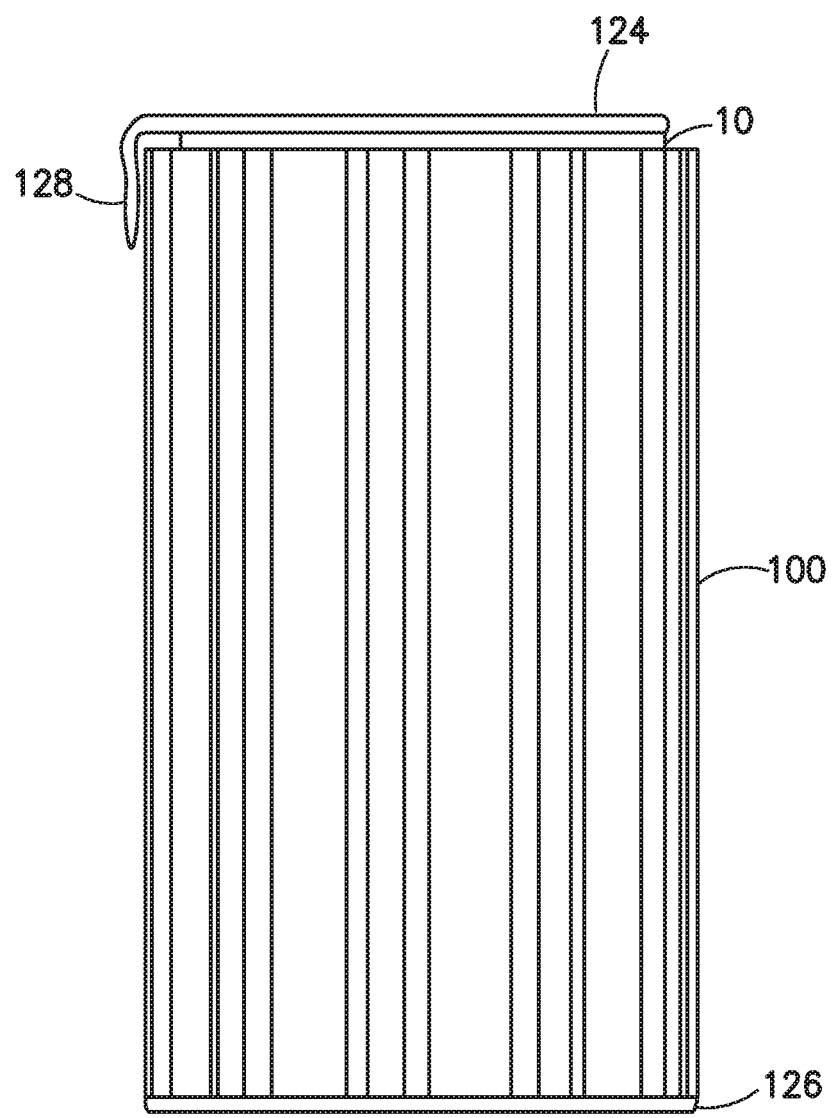
FIG. 13 is a side view of a sterility barrier in accordance with an embodiment of the present invention.

FIG. 13 is a side view of a sterility barrier in accordance with another embodiment of the present invention. As shown in FIG. 13, the sterility barrier includes a removable barrier 124 affixed to the non-patient end of the pen needle 10, and a non-removable or fixed barrier 126 on the opposing end of the cover 100. According to one embodiment, the removable barrier 124 includes a tab 128 for the user to grasp, to aid removal of the removable barrier 124. To access the pen needle 10, the user grasps the tab 128 and peels back the removable barrier 124, thereby exposing the non-patient end of the pen needle 10. Similar to previously-described embodiments, the user grasps the cover 100 while connecting the pen injector 50 to the pen needle 10. Also similar to previously-described embodiments, following the injection, the user grasps the cover 100, inserts the pen needle into the cover 100, and then disengages the pen injector 50 from the pen needle 10, for example, by unthreading.

Materials for the removable barrier 124 and the non-removable barrier 126 can include paper, plastic, foil, or a combination of materials. One skilled in the art will appreciate that the removable barrier 124 and the non-removable barrier 126 need not be made of the same material to be within the scope of the present invention. As an alternative to the depicted embodiment, the pen needle 10 can be inserted flush with the end of the cover 100, and the removable barrier 124 can be affixed to the end of the cover 100.

Figure 14:
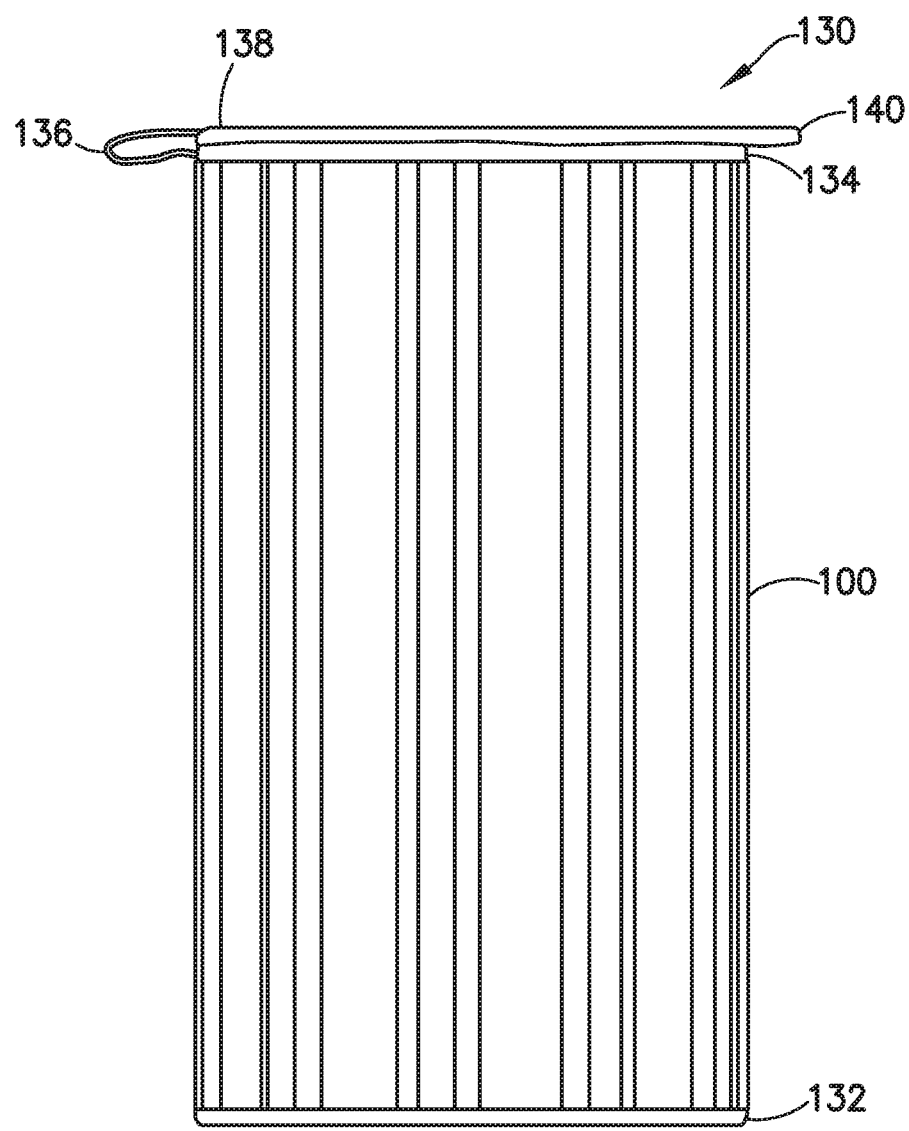
FIG. 14 is a is a side view of a sterility barrier in accordance with an embodiment of the present invention.

FIG. 14 is a side view of a sterility barrier in accordance with another embodiment of the present invention. As shown in FIG. 14, the sterility barrier includes a removable cap 130 attached to the non-patient end of the pen needle 10, and a non-removable or fixed cap 132 on the opposing end of the cover 100. According to one embodiment, the removable cap 130 includes a rim 134 fixedly connected to the cover 100, a lid 138, and a connector 136 connecting the rim 134 and the lid 138. According to one embodiment, the connector is a strip. Other connectors, such as a living hinge, can be used without departing from the scope of the present invention. Alternatively, the lid 138 can be directly connected to the cover 100, without a rim 134. Preferably, the lid 138 has a protruding lip 140 disposed thereon to aid the user in opening and closing the lid 138.

To access the non-patient end of the pen needle 10, the user grasps the cover 100, presses the lip 140, and rotates the lid 138. Then, by grasping the cover 100, the user can connect the pen injector to the pen needle 10 within the cover 100 as previously described. Subsequent to the injection, the user can return the used pen needle 10 to the cover 100 by grasping the cover 100, inserting the pen needle 10, and then disconnecting the pen injector 50 from the pen needle 10. The user can then close the lid 138. Materials for the removable cap 130 and the fixed cap 132 can include plastic or a combination of materials. One skilled in the art will appreciate that the removable cap 130 and the fixed cap 132 need not be made of the same material to be within the scope of the present invention.

Figure 15:
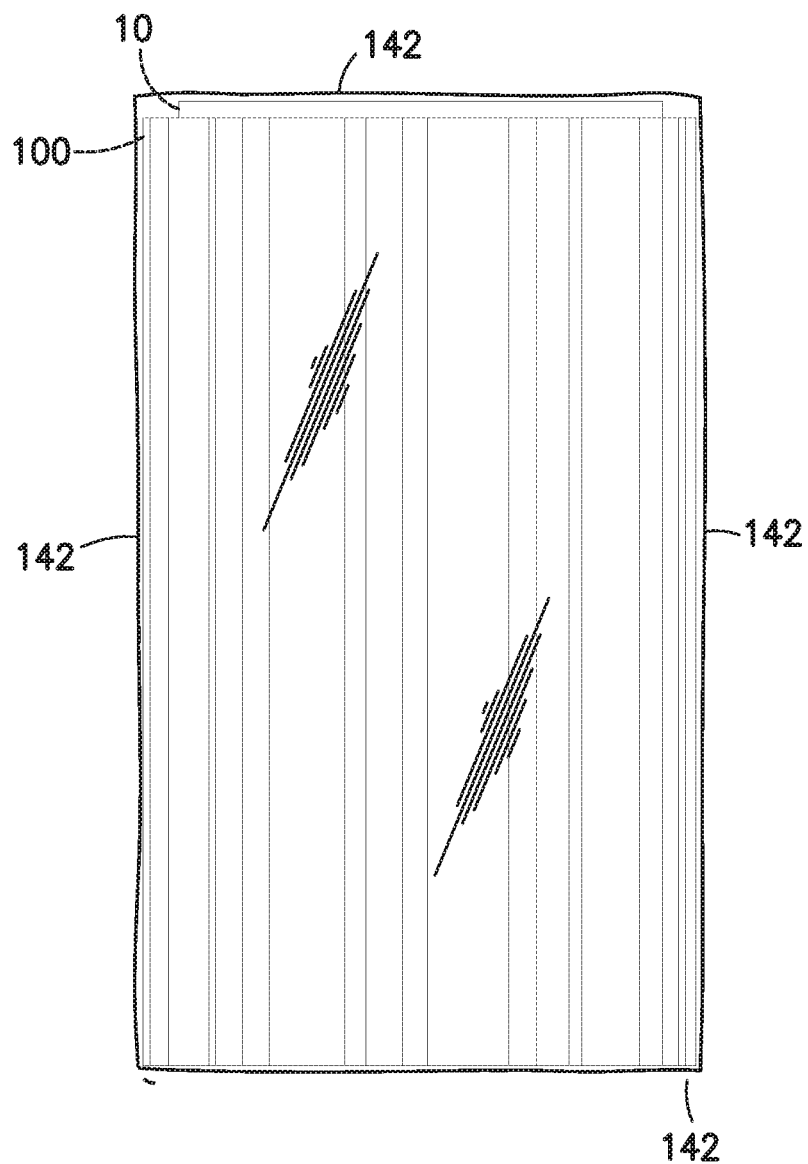
FIG. 15 is a side view of a sterility barrier in accordance with an embodiment of the present invention.

FIG. 15 is a side view of a sterility barrier 142 in accordance with another embodiment of the present invention. As shown in FIG. 15, the sterility barrier 142 includes a transparent plastic material tightly surrounding or encasing the entire periphery of the combined pen needle 10 and cover 100. According to one embodiment, the sterility barrier 142 is shrink-wrapped onto the combined pen needle 10 and cover 100. To access the pen needle 10, the user pierces the sterility barrier 142 to expose the non-patient end of the pen needle 10. Then, by grasping the cover 100, the user can connect the pen injector to the pen needle 10 as previously described. Subsequent to the injection, the user can return the used pen needle 10 to the cover 100 by grasping the cover 100, inserting the pen needle 10, and then disconnecting the pen injector 50 from the pen needle 10.

Although embodiments of the present invention have been described in relation to pen needles, it will be understood by one skilled in the art that other medical needles and cannulas with hubs can be packaged in the same or similar way. For example, an open-ended cover for a hypodermic needle can engage the hub of the hypodermic needle, and a sterility barrier in accordance with an embodiment of the present invention can then encase the cover and the hypodermic needle. Following removal or opening of the sterility barrier, the user can grasp the cover and/or the sterility barrier and connect a syringe to the hypodermic needle. After the injection, the user can grasp the cover and/or the sterility barrier, reinsert the hypodermic needle into the cover, and disconnect the syringe from the needle.

Another embodiment is contemplated, in which prior to the sterility barrier encasing the cover and the medical cannula, the injection device, for example, a syringe or a pen injector, can be connected to the medical cannula engaged in the cover. Thus when the sterility barrier encapsulates the cover and the medical cannula, the injection device is also encapsulated. In such an embodiment, the user removes or opens the sterility barrier, then separately grasps the cover and the injection device, pulls on the injection device to remove the medical cannula from the cover, thereby exposing the patient end of the medical cannula. Subsequent to the injection, the user can grasp the cover and reinsert the medical cannula into the cover, thereby protecting the patient end of the medical cannula and preventing accidental needle-stick injury.

Some embodiments of the present invention do not require the use of labels, such as label 32. Additionally, embodiments of the present invention do not require the use of an inner shield, such as inner shield 28. Therefore, embodiments of the present invention reduce the number of parts for sterile packaging of pen needles. Additionally, embodiments of the present invention may simplify the sterile packaging process of pen needles, and therefore increase the efficiency of such a process.

The present invention is not limited to use with sharpened medical cannulas such as pen needles and syringe needles. For example, blunt cannulas of the type used to inject medicaments into IV lines through split-septum injection sites can also be packaged as disclosed herein.

Although only a few embodiments of the present invention have been shown and described, the present invention is not limited to the described embodiments. Instead, it will be appreciated by those skilled in the art that changes may be made to these embodiments without departing from the principles and spirit of the invention as defined in the appended representative claims and their equivalents.

What is claimed is:

1. A method, comprising:
    providing a cover for receiving a medical cannula having a distal end and a hub, and for securing the hub of the medical cannula therein, the cover having open ends that are in communication through the cover, and a lock-out feature for preventing removal of a medical cannula after the medical cannula is inserted distally into the cover by a predetermined distance to engage the lockout feature;
    inserting the medical cannula into the cover to engage the cover; and
    providing a sterility barrier to cover both open ends of the cover with the medical cannula disposed therein.

2. The method according to claim 1, wherein inserting the medical cannula into the cover comprises inserting the medical cannula into the cover less than the predetermined distance.

3. The method according to claim 1, further comprising:
    removing the medical cannula from the cover; and
    reinserting the medical cannula into an open end of the cover distally so that the proximal end of the hub bypasses the lock-out feature;
    wherein the cover comprises a stop to prevent a medical cannula from being inserted so far into one of the open ends of the cover that a needle portion of the medical cannula presents a danger at the other open end of the cover.

4. The method according to claim 1, wherein a tolerance of a fit between the hub and the cover is adapted to ensure that a proximal end of the hub bypasses the lock-out feature upon application of a force by a user to insert the medical cannula into the cover.

5. A method, comprising:
    providing a medical cannula having a hub, the medical cannula also having a distal end for insertion into a patient;
    providing a cover for removably receiving the medical cannula in a first orientation and for securing therein the hub of the medical cannula, the cover:
        having open ends that are in communication through the cover; and
        having a lock-out feature for retaining the medical cannula within the cover after the medical cannula is inserted into the cover in the first orientation so that a proximal end of the hub distally bypasses the lock-out feature;
    inserting the medical cannula into the cover in the first orientation without the proximal end of the hub distally bypassing the lock-out feature so that the cover extends distally beyond the distal end of the medical cannula; and
    encasing the cover and the medical cannula with a sterility barrier.

6. The method according to claim 5, wherein the sterility barrier comprises:
    a blister pack, comprising:
        a blister portion for housing the cover and the medical cannula; and
        a lid portion for sealing the blister portion.

7. The method according to claim 6, further comprising:
    at least partially retaining the cover within the blister portion during connection and/or disconnection of a medical cannula with an injection device.

8. The method according to claim 7, wherein the blister portion comprises an internal rib to grasp the cover to retain the cover at least partially within the blister portion during connection of the medical cannula with the injection device.

9. The method according to claim 6, further comprising providing an array of packages, wherein perforations separate at least one package in the array.

10. The method according to claim 9, wherein at least one package is individually separable from the array.

11. The method according to claim 5, wherein the sterility barrier comprises an individually sealed wrapper.

12. The method according to claim 11, joining the sterility barriers longitudinally to form a strip.

13. The method according to claim 12, further comprising perforating the strip to separate the individual sterility barriers.

* * * * *